United States Patent [19]
Luu et al.

[11] Patent Number: 5,871,763
[45] Date of Patent: Feb. 16, 1999

[54] SUBSTRATE TREATED WITH LOTION

[75] Inventors: Phuong V. Luu; T. Philips Oriaran, both of Appleton; David W. White, Neenah; Anthony O. Awofeso, Appleton; Gary L. Schroeder, Neenah; Richard E. Fredricks, Appleton, all of Wis.

[73] Assignee: Fort James Corporation, Deerfield, Ill.

[21] Appl. No.: 847,409

[22] Filed: Apr. 24, 1997

[51] Int. Cl.[6] .................................................. A01N 25/34
[52] U.S. Cl. .......................................... 424/402; 424/404
[58] Field of Search ..................................... 424/402, 404

[56] References Cited

U.S. PATENT DOCUMENTS

| | | | |
|---|---|---|---|
| 3,619,280 | 11/1971 | Scheuer | 117/154 |
| 3,896,807 | 7/1975 | Buchalter | 128/261 |
| 4,112,167 | 9/1978 | Dake et al. | 428/154 |
| 4,351,699 | 9/1982 | Osborn | 162/112 |
| 4,441,962 | 4/1984 | Osborn | 162/111 |
| 4,462,981 | 7/1984 | Smith | 424/27 |
| 4,466,431 | 8/1984 | Tharrat et al. | 128/156 |
| 4,481,243 | 11/1984 | Allen | 428/154 |
| 4,513,051 | 4/1985 | Lavash | 428/212 |
| 4,550,035 | 10/1985 | Smith | 427/398.1 |
| 4,643,939 | 2/1987 | Sugiyama et al. | 428/283 |
| 4,690,821 | 9/1987 | Smith et al. | 424/401 |
| 4,741,944 | 5/1988 | Jackson et al. | 428/152 |
| 4,786,367 | 11/1988 | Bogart et al. | 162/158 |
| 4,806,572 | 2/1989 | Kellett et al. | 521/112 |
| 4,842,593 | 6/1989 | Jordan et al. | 604/360 |
| 4,882,221 | 11/1989 | Bogart et al. | 428/308.8 |
| 4,883,475 | 11/1989 | Bogart et al. | 604/290 |
| 4,940,513 | 7/1990 | Spendel et al. | 162/112 |
| 4,943,350 | 7/1990 | Bogart et al. | 162/158 |
| 4,990,340 | 2/1991 | Hidaka et al. | 424/449 |
| 5,055,216 | 10/1991 | Johnson | 252/91 |
| 5,156,843 | 10/1992 | Leong et al. | 428/446 |
| 5,227,242 | 7/1993 | Walter et al. | 424/411 |
| 5,240,562 | 8/1993 | Phan et al. | 162/158 |
| 5,246,545 | 9/1993 | Ampulski et al. | 162/112 |

(List continued on next page.)

FOREIGN PATENT DOCUMENTS

| | | |
|---|---|---|
| 0365726 | 5/1990 | European Pat. Off. . |
| 2066661 | 7/1981 | United Kingdom . |
| WO 95/16824 | 6/1995 | WIPO . |
| WO 95/35411 | 12/1995 | WIPO . |
| WO 95/35412 | 12/1995 | WIPO . |
| WO 96/19204 | 6/1996 | WIPO . |
| WO 96/24329 | 8/1996 | WIPO . |
| WO 96/24722 | 8/1996 | WIPO . |
| WO 96/24723 | 8/1996 | WIPO . |
| WO 97/16066 | 5/1997 | WIPO . |

*Primary Examiner*—Thurman K. Page
*Assistant Examiner*—Kathryne E. Shelborne

[57] ABSTRACT

A substrate treated with a lotion including an emollient and a retention/release agent, wherein the lotion has at least one of: (a) a ΔH above about 37° C. of above about 10 calories/gram (and optionally, a ΔH below about 37° C. of above about 15 calories/gram), a total heat of melting of above about 25 calories/gram, preferably above about 30 calories/gram, and an onset of melting temperature of at least about 30° C., preferably from about 30° C. to about 45° C.; and (b) a ΔH above about 30° C. of above about 15 calories/gram (and optionally, a ΔH below about 30° C. of above about 10 calories/gram), a total heat of melting of above about 25 calories/gram, preferably above about 30 calories/gram, and an onset of melting temperature of at least about 30° C., preferably from about 30° C. to about 45° C. is disclosed. Preferably the lotion includes an aromatic ester or fatty alcohol ester of a non-fatty organic acid emollient or mixture thereof and a retention/release agent, and optionally, surfactant, and/or medicinal agent. The lotion has the effect of making the treated substrate, preferably tissue, towel or napkin, optionally wet-strengthened, wipe or nonwoven material, feel smooth, lubricious and nongreasy. The skin care benefits of the lotionized substrate are expressed whether the product is used dry or prewetted with water.

75 Claims, 2 Drawing Sheet

U.S. PATENT DOCUMENTS

| | | | |
|---|---|---|---|
| 5,262,007 | 11/1993 | Phan et al. | 162/158 |
| 5,264,082 | 11/1993 | Phan et al. | 162/158 |
| 5,362,488 | 11/1994 | Sibley et al. | 424/78.05 |
| 5,372,739 | 12/1994 | Neal et al. | 252/8.6 |
| 5,415,737 | 5/1995 | Phan et al. | 162/111 |
| 5,473,059 | 12/1995 | Yeh | 536/18.7 |
| 5,520,908 | 5/1996 | Lundmark | 424/70.1 |
| 5,525,345 | 6/1996 | Warner et al. | 424/402 |
| 5,547,661 | 8/1996 | Sun et al. | 424/66 |
| 5,562,642 | 10/1996 | Smith et al. | 604/289 |
| 5,567,427 | 10/1996 | Papadakis | 424/401 |
| 5,573,637 | 11/1996 | Ampulski et al. | 162/112 |
| 5,607,760 | 3/1997 | Roe | 604/360 |
| 5,607,980 | 3/1997 | McAtee et al. | 514/476 |
| 5,609,587 | 3/1997 | Roe | 442/375 |
| 5,614,293 | 3/1997 | Krzysik et al. | 428/211 |
| 5,624,676 | 4/1997 | Mackey et al. | 424/414 |
| 5,643,588 | 7/1997 | Roe et al. | 604/360 |
| 5,650,144 | 7/1997 | Hofrichter et al. | 162/112 |
| 5,650,218 | 7/1997 | Krzysik et al. | 424/211 |
| 5,665,426 | 9/1997 | Krzysik et al. | 427/211 |
| 5,716,692 | 2/1998 | Warner et al. | 428/153 |
| 5,720,966 | 2/1998 | Ostendorf et al. | 424/402 s |

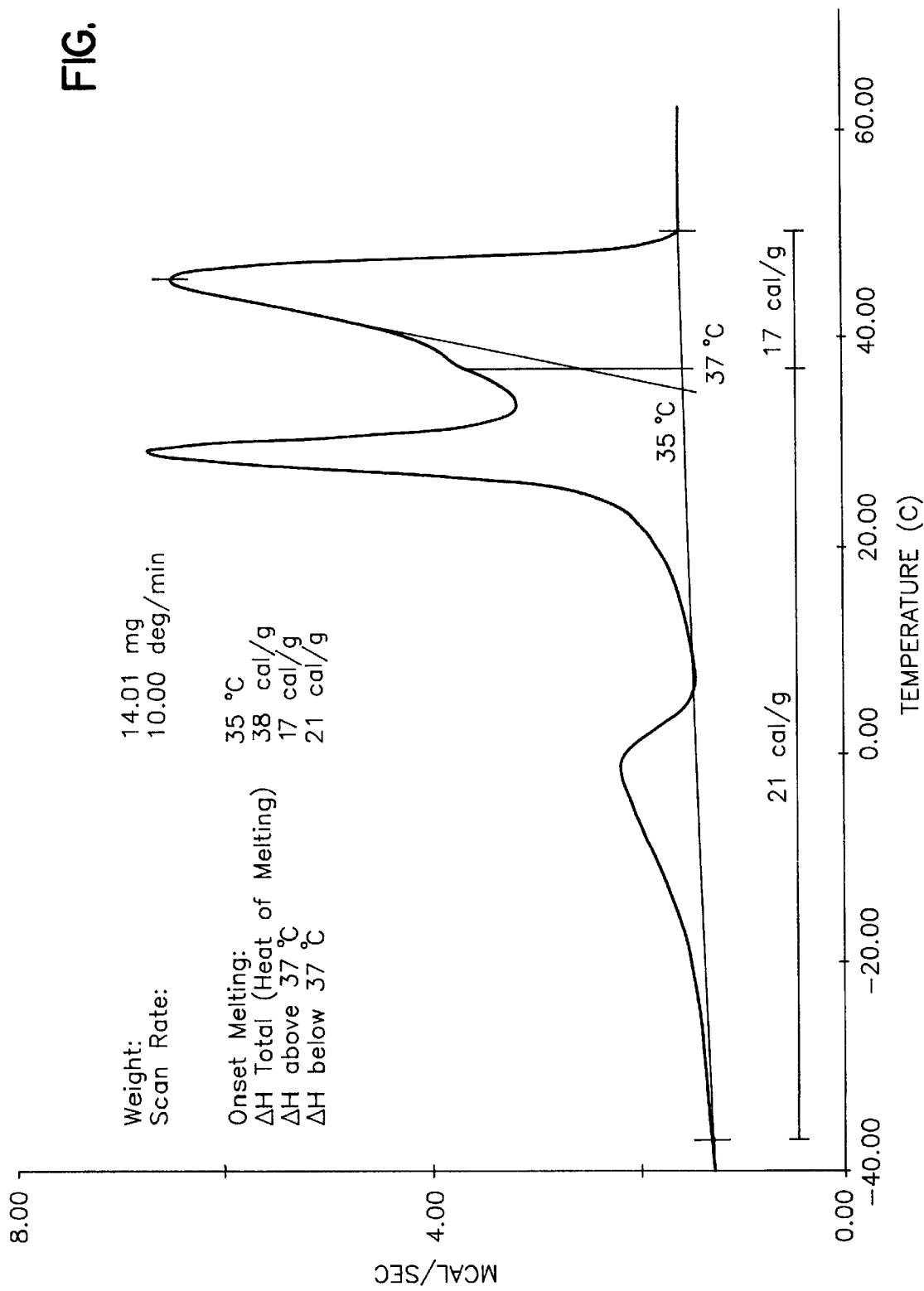

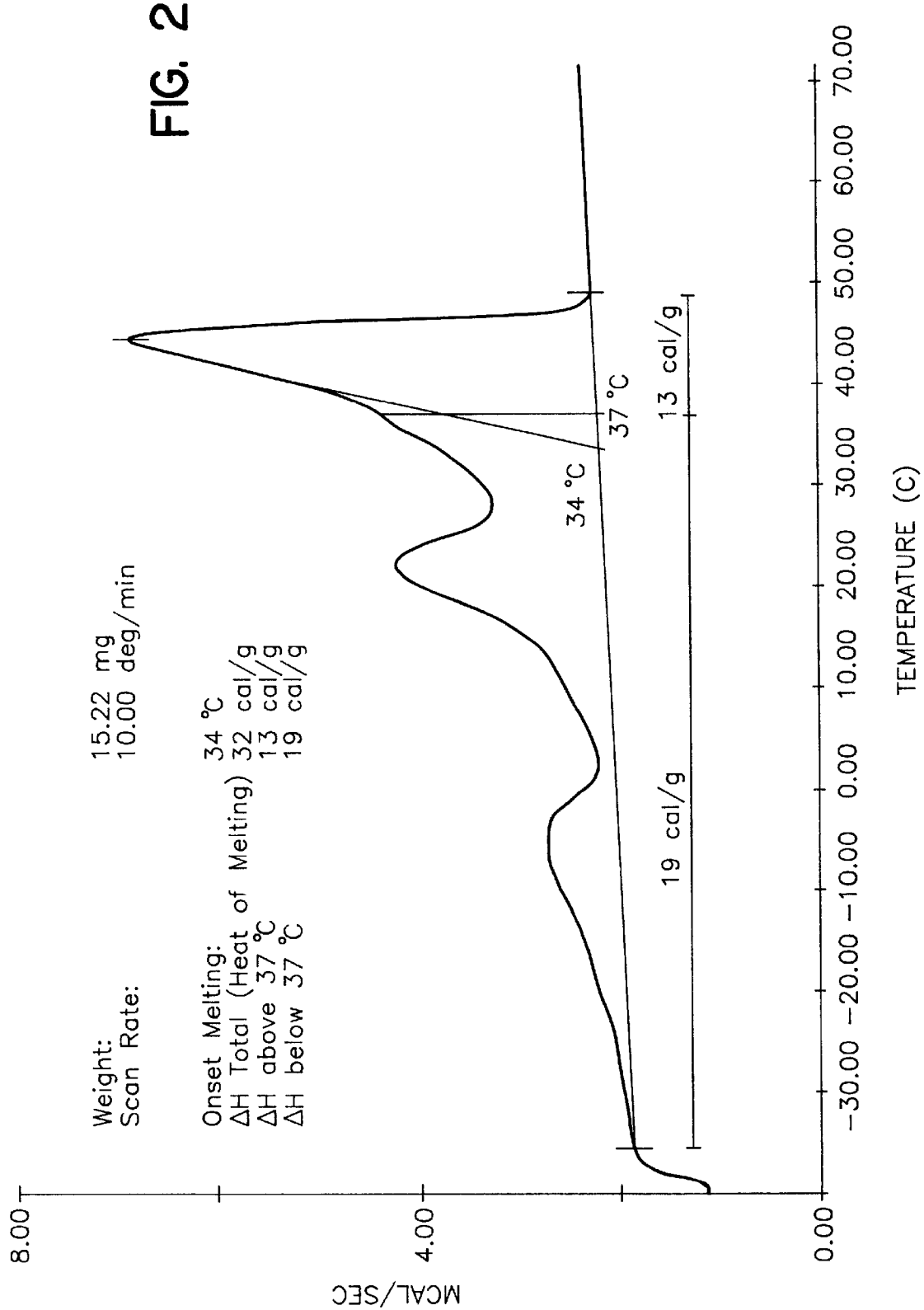

SUBSTRATE TREATED WITH LOTION

BACKGROUND OF THE INVENTION

1. Field of the Invention

This invention relates to a substrate treated with lotion. In particular, this invention relates to a nongreasy-feeling lotionized substrate whereby the lotion transfers to the skin during use to provide a smooth, lubricious, nongreasy-feeling layer on the skin. The nongreasy-feeling lotion contains an emollient and retention/release agent. The lotion may also contain optional ingredients, including a surfactant and/or a medicinal agent.

2. Description of the Related Art

Absorbent tissue and towel products, such as facial tissue, bath tissue and paper towels, wipes and nonwoven materials have been used to absorb body fluids and cleanse and dry the skin. Absorbent products such as these have the disadvantage of abrading and drying out the skin causing uncomfortable irritation and redness. To reduce these deleterious effects, the substrate has been provided with formulations, which have lubricity thereby enabling the substrate to glide across the surface of the skin, or which become deposited on the surface of the skin in an attempt to replenish lost natural skin oils.

Examples of lotionized bathroom and facial tissue include Charmin Plus® and Puffs Plus®, respectively, commercially available from the Procter & Gamble Co. These products contain a lotion based on petrolatum and mineral oil and leave a greasy feel to the skin after use.

Kleenex Ultra®, made by the Kimberly-Clark Corp., is an example of a commercially available facial tissue treated with a silicone-based lotion in an effort to render the tissue smoother feeling and softer. U.S. Pat. No. 5,227,242 to Walter et al., discloses facial tissues containing a silicone compound represented as exhibiting improved softness and reduced linting while maintaining absorbency.

Numerous examples of premoistened wipes can be found in the marketplace. However, many of these contain volatile alcohol solutions which remove skin lipids and fats, causing dryness, and do not provide a lubricious nongreasy-feeling layer on the skin.

U.S. Pat. No. 4,550,035 to Smith relates to cosmetic applicators which include an absorbent sheet impregnated with a complex mixture of emollients, absorbent particles, fragrances and deodorizing agents. The emollients may include emollient oils, such as fatty alcohol esters of benzoic acid, col. 2, line 64, and a mixture of $C_{12}$–$C_{15}$ linear primary alkyl esters of benzoic acid such as FINSOLV® TN, col. 3, lines 8–13; emollient waxes, such as $C_{12}$–$C_{18}$ fatty-alcohols, col.3, line 20; cationic emollients; and nonionic emollients.

U.S. Pat. No. 4,690,821 to Smith et al., discloses the simultaneous moisturizing and absorbing of water from wet skin with cosmetic applicators impregnated with a water-free composition including a hydrophilic emollient oil and a hydrophobic emollient oil. The combination of benzyl alcohol ester of a $C_{10}$–$C_{20}$ fatty acid with fatty alcohol esters of benzoic acid, such as $C_{12}$–$C_{15}$ alkyl benzoate (FINSOLV® TN), provides a hydrophobic emollient oil. The fatty alcohol benzoates can be replaced by waxy $C_2$–$C_5$ alkyl esters of fatty acids or fatty alcohol esters of $C_3$–$C_6$ aliphatic carboxylic acids. A hydrophilic emollient oil is disclosed which includes a $C_2$–$C_{10}$ polyol having 2–5 free hydroxyl groups reacted with a fatty acid, fatty alcohol or a polyoxy (lower) alcohol plus lanolin derivative of polyoxyalkylene and a polyoxyalkylene derivative of a fatty alcohol.

European Applications WO95/35411 and WO95/35412 to Klofta, et al., disclose a lotioned tissue paper represented as imparting a soft, lubricious, lotion-like feel. The lotioned tissue paper contains a lotion composition which is semi-solid or solid at 20° C. The lotion composition contains a substantially water free emollient having a plastic or fluid consistency at 20° C. and being a member selected from petroleum-based emollients, fatty acid ester emollients, alkyl ethoxylate emollients, fatty acid ester ethoxylates, fatty alcohol emollients, and mixtures thereof; an agent capable of immobilizing the emollient on the surface of the tissue paper, the immobilizing agent having a melting point of at least 35° C. and being a member selected from $C_{12}$–$C_{22}$ fatty alcohols, $C_{12}$–$C_{22}$ fatty acids, $C_{12}$–$C_{22}$ fatty alcohol ethoxylates, and mixtures thereof; and optionally a hydrophilic surfactant.

U.S. Pat. No. 4,112,167 to Dake, et al., discloses an article of manufacture for cleansing the skin. A soft, flexible web having a low density wiping zone works in concert with a lipophilic cleansing emollient in an effort to remove soil from the skin with improved effectiveness. It is represented that the lipophilic cleansing emollient reduces hydration of the soil and weakens the soil-skin adhesive forces while the low density wiping zone of the web entraps and thus removes the soil from the skin.

European Application WO95/16824 to Warner et al., discloses a lotion represented as imparting a lubricious, lotion-like feel when applied to tissue paper in amounts as low as 5–15% by weight. The lotion includes plastic or fluid emollient such as petrolatum, or a mixture of petrolatum with alkyl ethoxylate emollient, and an immobilizing agent such as sorbitan stearates or N-coco, N-methyl glucamide to retain the lotion on the surface of the tissue and optionally a hydrophilic surfactant to improve wettability. Less lotion is applied than other lotionized tissue in an effort to minimize detrimental effects on tensile strength and caliper of treated tissue.

U.S. Pat. No. 4,643,939 to Sugiyama et al., relates to an oil absorbing cosmetic tissue consisting of an absorbent sheet impregnated with a bactericide, such as triclosan (col. 2, line 46). This tissue is designed to absorb oil rather than to transfer a lotion to the skin.

Thus, there is a need for a lotion formulation that can be applied to a substrate which will remain readily available for transfer to the user's skin in an efficient and cost-effective manner, which provides a lubricious, nongreasy-feeling and breathable layer which maintains proper skin moisture/vapor balance, which users may find soothing to irritated skin and which may facilitate healing of chapped skin and skin suffering from discomfort, such as diaper rash or hemorrhoids.

SUMMARY OF THE INVENTION

The present invention relates to a substrate treated with a nongreasy-feeling lotion containing an emollient and a retention/release agent as base ingredients. The lotion has the effect of making the treated substrate feel nongreasy and lubricious. Skin care benefits of the lotionized substrate are expressed whether the product is used dry or prewetted with water.

Thus, in accordance with one aspect of the present invention, there is provided a lubricious, nongreasy-feeling lotionized tissue, wipe or nonwoven material, whereby the lotion transfers to the skin during use to provide a breathable, smooth layer which acts to maintain the proper skin moisture/vapor balance and which users find soothing to irritated or damaged skin.

In accordance with another aspect of the present invention, there is provided a substrate treated with a lotion which, optionally, contains one or more of the following: a surfactant which aids in skin cleansing, and a medicinal agent, such as an antimicrobial agent which kills bacteria and fungi commonly found on skin, thereby providing an enhanced cleaning and deodorizing benefit.

In accordance with a further aspect of the present invention, there is provided a tissue, towel or napkin, optionally wet-strengthened, or wipe or nonwoven material, such as that used for diaper, incontinence and menstrual pad coverstock, that is treated with a nongreasy-feeling lotion.

In accordance with a still further aspect of the present invention, there is provided an embossed tissue, embossed towel, or embossed napkin, optionally wet-strengthened, that is treated with a nongreasy-feeling lotion.

In accordance with yet another aspect of the present invention, there is provided a lubricious, nongreasy-feeling lotionized tissue, wipe or nonwoven material, whereby the lotion forms a cold cream when contacted with water and transfers to the skin during use to provide a breathable, smooth layer which acts to maintain the proper skin moisture/vapor balance and which users find soothing to irritated or damaged skin.

BRIEF DESCRIPTION OF THE DRAWINGS

These and other aspects of the present invention will become apparent upon a review of the following detailed description and accompanying drawings wherein:

FIG. 1 is a DSC thermogram plot of the melting properties of a lotion formulation of the invention; and FIG. 2 is a DSC thermogram plot of the melting properties of a lotion formulation of the invention.

DETAILED DESCRIPTION OF PREFERRED EMBODIMENTS

All percentages, ratios and proportions used herein are by weight of the composition, unless otherwise specified. The temperature of human skin is assumed to be between about 30° C. and about 37° C. and room temperature is assumed to be between about 20° C. and about 25° C.

The present invention relates to a substrate treated with a nongreasy-feeling lotion. The invention also relates to a tissue, towel or napkin, optionally wet-strengthened, or wipe or nonwoven material, such as that used for diaper, incontinence and menstrual pad coverstock that is treated with a nongreasy-feeling lotion. The lotion has the effect of making the treated substrate feel nongreasy, reducing chaffing and irritation when the substrate is applied to the skin, and imparting a lubricious feel. Skin care benefits of the lotionized substrate are expressed whether the invention is used dry or prewetted with water.

The lotion formulation possesses desired physical attributes, such as having a smooth, lubricious, nongreasy feel; the ability to form a breathable layer which acts to maintain proper skin moisture/vapor balance; the ability to moisturize the skin; the ability when melted to wet the surface of the substrate; the capability to be retained on a substrate at about room temperature; and the ability to at least partially melt to transfer to the surface of the skin when contact is made with body heat. After transfer, at least a portion of the lotion may resolidify on the skin to form a smooth surface layer that is perceived as nongreasy.

Most preferably, the lotion is substantially free of water, i.e., anhydrous. Preferably, water is not intentionally added to the lotion. However, minor amounts of water may be present due to ambient humidity or small amounts added with optional additives. Typically, the lotion of the present invention contains about 15% or less water, preferably about 10% or less water, more preferably about 5% or less water.

An advantage in formulating a water-free, or low water content lotion includes the improved storage and handling characteristics of such lotions. Under anhydrous or low water content conditions, microorganism growth is reduced. However, as the water content increases, microorganisms can proliferate by using the organic ingredients as nutrient sources. Under such circumstances, suppression of microbial growth typically requires the addition of preservation agents. Furthermore, as the water content of oil-based lotions increases, the water forms droplets suspended in the matrix of "oily" ingredients. At low water levels these droplets are able to move freely past each other during mixing of the lotion. As the amount of water is increased, the number and size of water droplets increases, leading to crowding of the available space for the droplets to move about. This crowding is reflected in an increased viscosity of the lotion. Of course, viscosity modifiers known to those skilled in the art can be added to control viscosity.

The present invention relates to a substrate treated with a nongreasy-feeling lotion containing an emollient and a retention/release agent as base ingredients. The lotion may also contain one or more optional ingredients, which include the following: a mild surfactant which facilitates skin cleansing, and a medicinal agent such as an antimicrobial agent which kills bacteria, virus, protozoa and fungi commonly found on skin thereby providing an enhanced cleaning and deodorizing benefit.

The lotion of the present invention has a $\Delta H$ above about 37° C. of above about 10 calories/gram and a $\Delta H$ total (total energy to melt) of above about 25 calories/gram, preferably above about 30 calories/gram.

In another embodiment, the lotion of the present invention has a $\Delta H$ below about 37° C. of above about 15 calories/gram, a $\Delta H$ above about 37° C. of above about 10 calories/gram, and a $\Delta H$ total (total energy to melt) of above about 25 calories/gram, preferably above about 30 calories/gram.

In another embodiment, the lotion of the present invention has a $\Delta H$ above about 30° C. of above about 15 calories/gram and a $\Delta H$ total (total energy to melt) of above about 25 calories/gram, preferably above about 30 calories/gram.

In another embodiment, the lotion of the present invention has a $\Delta H$ above about 30° C. of above about 15 calories/gram, a $\Delta H$ below about 30° C. of above about 10 calories/gram, and a $\Delta H$ total (total energy to melt) of above about 25 calories/gram, preferably above about 30 calories/gram.

A lotion that meets at least one of these energy melting criteria is perceived as nongreasy, having high quality performance and hand feel perception.

Additionally, the lotion of the present invention has an onset of melting for the highest melting peak of the lotion formulation of above about 30° C. The onset of melting temperature, as used herein, is defined as the point at which the highest melting Differential Scanning Calorimetry (DSC) endothermic peak begins to transition from the solid to the liquid phase. The onset of melting temperature is determined by the point at which a tangent drawn at the greatest slope on the leading edge of the endothermic peak intersects the extrapolated baseline of the DSC thermogram. This point of intersection has also been called the extrapolated onset. See, for example, "Thermal Analysis, 3rd Edition", by Wendlandtt, which is incorporated by reference herein in its entirety. Typically, this peak represents the melting of the retention/release agent ingredient of the lotion formulation. Consequently, the onset of melting temperature of the lotion is typically lower than the onset of melting temperature of the retention/release agent alone, due to the melting point depression of the retention/release agent caused by the emollient and any optional ingredients in the lotion. Preferably, the onset of melting temperature of the lotion is within the range of from about 30° C. to about 45° C., more preferably, within the range that approximates skin temperature.

Thus, both the onset of melting temperature and the energy required to melt the lotion are important to hand feel perception. Data in Tables 3 and 4 show that the energy required to melt the entire lotion formulation (ΔH total), the ΔH below about skin temperature (e.g., represented by ΔH values obtained below about 30° C. and below about 37° C.), as well as the ΔH above about skin temperature (ΔH above about 30° C. and ΔH above about 37° C.) are correlated to the "Greasiness Index." In general, if the total energy required to melt a lotion is too low, the lotion tends to be completely melted to a liquid by body heat at the moment it is transferred from the substrate to the skin and is perceived as greasy. Moreover, a lotion having too high a total energy to melt that will not be partially melted by body heat is also an undesirable lotion because it will not spread easily on the skin. Such undesirable lotions do not transfer sufficient desired materials to the skin, and they have a dry feel. The preferred lotion is partially melted by body heat, transfers to the skin upon application and at least a portion of the lotion resolidifies on the skin to form a silky smooth layer that is perceived as nongreasy. It is thought that the lotion of the present invention can be viewed at about skin temperature as a layer of solid retention/release agent particles, at least partially liquefied emollient(s), the liquefied portion of the retention/release agent, and possibly liquefied and/or solid optional ingredients, and that this structure provides an effect that enhances lubricity and nongreasy hand feel perception. Skin application and post application temperatures may fluctuate due to frictional forces during application and environmental factors which may cause components of the lotion formulation to undergo slight changes in the proportions of liquid and solid phase components of the formulation.

FIG. 1 illustrates the melting properties of the lotion formulation of Example 6. The highest melting peak in FIG. 1 exhibits an onset of melting at about 35° C., confirming that this lotion is partially melted at about human skin temperature.

FIG. 2 illustrates the melting properties of the lotion formulation of Example 21. The highest melting peak in FIG. 2 exhibits an onset of melting at about 34° C., confirming that this lotion is partially melted at about human skin temperature.

The retention/release agent is present in an amount of preferably from about 25% to about 95%, more preferably from about 45% to about 90% of the lotion. The retention/release agent has two functions. First, it functions as a retention aid for the emollient (or emollient blend) and the optional lotion ingredients on the substrate. When liquid, the lotion formulation has a surface tension that allows it to wet the substrate. Second, it functions to facilitate release from the substrate of the emollient (or emollient blend and optional ingredients when the treated substrate is applied to human skin. Retention of the ingredients of the lotion formulation on the substrate is facilitated by the retention/release agent as the retention/release agent is preferably selected to have a melting point substantially higher than about room temperature. This enables the lotion formulation to be maintained substantially as a solid at about room temperature. At about human skin temperature, the lotion at least partially melts to transfer at least a portion of the emollient (or emollient blend), retention/release agent, and optional ingredients as a layer on the skin. After transfer at least a portion of the liquid retention/release agent may resolidify together with other ingredients to provide a layer having a smooth, lubricious and nongreasy feel.

An important attribute of the retention/release agent is its melting properties, including its onset melting point. Preferably, the onset of melting of the retention/release agent is below about 50° C. (data collected using DSC). This allows melting point depression by the added emollient (or emollient blend) and optional ingredients to adjust the onset of melting for the highest melting peak of the lotion formulation to above about 30° C. Two or more retention/release agents can be blended in varying proportions to attain an onset of melting of the retention/release blend of less than about 50° C., as demonstrated in the examples provided in Table 1. The proportion of each component may depend on individual onsets of melting. As demonstrated in the Table 1, blending two or more retention/release agents may result in a blend with a lower heat of melting than for either of the components alone, resulting in an retention/release agent that will melt more easily on human skin.

Suitable retention/release agents include known agents, which when mixed with the emollient of the invention provide a lotion which has the above recited ΔH values and onset melting temperature of the present lotion. Suitable retention/release agents are those agents capable of facilitating the retention of the lotion on the substrate to which the lotion is applied and facilitating the release of the lotion from the substrate when applied to the skin. It is noted that the melted lotion formulation of the present invention has surface tension values such that the lotion is capable of wetting the substrate and when cooled is capable of being retained on the substrate. Similarly, the lotion formulation of the present invention has surface tension values when at least partially melted such that the lotion is capable of being transferred to the skin upon contact. Preferably, retention/release agents include those agents, which when mixed with the emollient of the invention, that are capable of imparting to the lotion the properties of being at least partially solid at about room temperature and which facilitate the retention of the lotion on the substrate at about room temperature and at least partially liquid at about human skin temperature and which facilitate the release of the lotion from the substrate at about human skin temperature. Suitable retention/release agents (or agent blends) include those retention/release agents (or blends) having an onset of melting temperature preferably between about 30° C. and about 65° C.

Fatty alcohols are suitable retention/release agents. Suitable fatty alcohols include substituted and unsubstituted, linear or branched $C_{10}$–$C_{24}$ fatty alcohols, preferably $C_{12}$–$C_{18}$ fatty alcohols. Preferred are dodecanols, tridecanols, tetradecanols, pentadecanols, hexadecanols, heptadecanols, octadecanols, nonadecanols, eicosanols, heneicosanols, docosanols, tricosanols, tetracosanols and mixtures thereof. Particularly preferred are cetyl alcohol, stearyl alcohol and cetearyl alcohol (which is a mixture of cetyl and stearyl alcohols).

Other retention/release agents include polymers having an appropriate melting range, such as poly(ethylene glycol) of 900 molecular weight or higher, low molecular weight natural and modified polysaccharides, vinyl ether maleic anhydride copolymers, polyacrylic acids, and polyvinyl pyrrolidones, or waxes, such as, beeswax, candelilla wax, carnuba wax, ceresine wax, montan wax, sugar cane wax, a commercial soft wax, and the like.

The fatty alcohols (or other retention/release agents) may be blended with behentrimonium methosulfate, stearalkonium chloride, PEG-40 castor oil, or mixtures thereof. The retention/release agents listed in Table 1 are not meant to limit the choices for the lotion of this invention.

TABLE 1

| Retention/Release Agent (or Blend) | Supplier Source | Onset of Melting (°C.) | ΔH total in calories per Gram |
|---|---|---|---|
| 1-Hexadecanol (H) | Aldrich Chemical | 48 | 55 |
| 1-Octadecanol (O) | Aldrich Chemical | 56 | 53 |
| Crodacol ® CS50 (50/50 Blend of H/O) | Croda Chemical | 49 | 49 |
| Crodacol ® C70 (70/30 Blend of H/O) | Croda Chemical | 47 | 49 |
| Crodacol ® S70 (70/30 Blend of O/H) | Croda Chemical | 50 | 49 |
| Incroquat ® Behenyl TMS * | Croda Chemical | 45 | 38 |
| Incroquat ® CR ** | Croda Chemical | 46 | 39 |

* A blend of 75% Crodacol ® CS50 with 25% behentrimonium methosulfate.
** A blend of 86% Crodacol ® CS50 with 7% PEG-40 castor oil and 7% stearalkonium chloride.

Suitable emollients of the present invention include emollients or emollient blends typically known in the art, or other compounds, or materials which function to lubricate or moisturize the skin surface, retard moisture loss, and/or maintain the skin moisture/vapor balance. Suitable emollients include those compounds which associate with the resolidified lotion to form a smooth, lubricious, nongreasy-feeling layer on the skin. Suitable emollients include those typically used in emollient creams and lotions, including liquid hydrocarbons (such as mineral oil, and the like), vegetable and animal fats and oils (such as, lanolin, triglycerides, and the like), alkyl fatty acid esters (such as methyl, isopropyl, and butyl esters of fatty acids, and the like), fatty alcohol esters of benzoic acid, phospholipids (such as lecithin, and the like), and silicones.

Preferably the emollients are liquid at or near human skin temperature, typically between about 30° C. and about 37° C., and when spread as a film, maintain the skin moisture/vapor balance. Preferably, emollients or emollient blends have complete and rapid spreading on water, i.e., have a high spreading ratio. A correlation has been discovered between emollients having a high spreading ratio on water and lotion formulations containing such emollients that have a less greasy or nongreasy hand feel perception by sensory panels. Additionally, the ability of the emollient to spread as a film provides a more breathable layer than nonspreading emollients, like petrolatum or mineral oil (or mixtures thereof). The spreading ratio is defined as the ratio of area occupied by a drop of the test emollient or emollient blend on a water surface over the area occupied by a drop of mineral oil on the water surface. Details of the test method can be found in "The Spreading Properties of Some New Liquid Emollients" by Rosemarie Pasquale, et. al. in the Journal of Cosmetics and Toiletries, October, 1985, which is incorporated herein by reference in its entirety.

The spreading behavior of nonspreading emollients, like mineral oil, can be modified to spread completely, as for example, by blending two or more emollients (see Table 2). The emollients or emollient blends listed in Table 2 are not meant to limit the emollients or emollient blends suitable for use in the lotion of this invention. Other emollients or emollient blends are suitable for the lotion of this invention, preferably those that are mostly liquid at about 30° C. and have a high spreading ratio on water. However, other emollients or emollient blends are suitable such as those not having a high spreading ratio and/or not being mostly liquid at about 30° C.

TABLE 2

| Emollient Blend # | Emollient Blend Composition | Spreading Ratio at 25° C. |
|---|---|---|
| 1 | mineral oil | 1 |
| 2 | C12-C15 alkyl octanoate | >35 |
| 3 | C12-C15 alkyl benzoate | >35 |
| 4 | 50% mineral oil/ 50% C12-C15 alkyl octanoate | >35 |
| 5 | 50% mineral oil/ 50% C12-C15 alkyl benzoate | >35 |
| 6 | 75% mineral oil/ 25% n-stearyl benzoate | >35 |

In another embodiment, the present invention relates to a substrate treated with a lotion including an aromatic ester emollient or fatty alcohol ester of a non-fatty organic acid emollient or mixture thereof and a retention/release agent, wherein the lotion is at least partially liquid at about human skin temperature and at least partially solid at about room temperature. The aromatic ester emollient or fatty alcohol ester of a non-fatty organic acid emollient or mixture thereof is present in an amount of at least about 5%, preferably, from about 5% to about 75%, more preferably from about 10% to about 55%, most preferably from about 15% to about 40% of the lotion. With respect to the present invention, the term "fatty" means a branched or unbranched non-aromatic, non-cyclic hydrocarbon chain having ten or more carbon atoms. The term "non-fatty" means a hydrocarbon chain having less than ten carbon atoms.

Suitable aromatic ester emollients of the invention include an ester containing at least one aromatic ring, preferably at most two aromatic rings. Suitable aromatic esters include benzoate esters, and esters of other aromatic acids, and mixtures thereof. Suitable benzoate ester emollients include $C_{12}$–$C_{15}$ alkyl benzoate, stearyl benzoate, octyl dodecyl benzoate, isostearyl benzoate, methyl gluceth-20 benzoate, stearyl ether benzoate, poloxamer 182 dibenzoate behenyl benzoate, poloxamer 105 benzoate, dipropylene glycol dibenzoate, or mixtures thereof. $C_{12}$–$C_{15}$ alkyl benzoate is a particularly preferred benzoate ester emollient.

Suitable emollients also include a fatty alcohol ester of a non-fatty organic acid, which include stearyl octanoate, cetyl octanoate, myristyl octanoate, lauryl octanoate, $C_{12}$–$C_{15}$ octanoate, triisocetyl citrate, isodecyl neopentanoate, isostearyl neopentanoate, and the like.

The lotion can also contain a surfactant which emulsifies the lotion when the lotion is combined with water during use to form a cream. Suitable surfactants include conventional surfactants, preferably cationic, anionic, nonionic, polymeric, amphoteric surfactants or mixtures thereof. In this manner various oil-in-water or water-in-oil emulsions can be created upon use. The surfactant may have a hydrophilic lipophilic balance (HLB) value of less than about 8. Alternately, the surfactant may have an HLB value of greater than about 13. Also known to the art is the blending of surfactants to obtain a desired range of HLB values. Preferably, the surfactant is a blend of from about 1% to about 10%, preferably from about 1% to about 3%, of a surfactant having an HLB value of less than about 8 and from about 1% to about 20%, preferably from about 1% to about 10%, of a surfactant having an HLB value of greater than about 13. Preferably, the surfactant blend is from about 5% to about 20%, most preferably from about 5% to about 15% of the lotion formulation. The surfactant having an HLB value of less than about 8 is preferably selected from the class of polyol esters, most preferably methyl glucoside sesquistearate. The surfactant having an HLB value of greater than about 13 is preferably selected from the class of ethoxylated polyol esters, wherein the ethoxylated polyol esters contain from 15 to 30 oxyethylene units, most preferably wherein the surfactant is ethoxylated methyl glucoside sesquistearate containing 20 moles of oxyethylene units.

The lotion can optionally include a therapeutic amount of a medicinal agent. Medicinal agents include medicines, antipathogenic agents, antimicrobial agents, antibacterial agents, antiviral agents, disinfectants, analgesics, other types of medicine having suitable medicinal properties, and the like. For example, an antibacterial agent can be present in an amount of from about 0.01% to about 10%, preferably from about 0.05% to about 5%, of the lotion. Suitable antimicrobial agents include those effective against human pathogens, such as *escherichia coli, staphylococcus aureus, salmonella chloreraesuis, salmonella typhi, pseudomonas aeruginosa, pseudomonas cepacia*, and the candida species, including albicans. Specific antimicrobial agents suitable for use in the lotion of the invention include 2,4,4'-trichloro-2'-hydroxydiphenyl ether (triclosan); 3,4,4'-trichlorocarbanilide (triclocarban); 3,4,4'-trifluoromethyl-4,4'-dichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol (chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; chlorhexidine gluconate; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; quaternary ammonium compounds, such as coco phosphatidyl PG-dimonium chloride; mixtures thereof; and the like. Other preferred antimicrobial agents include derivatives of substituted N-alkyl imidazolines disclosed in U.S. Pat. No. 4,078,071 to Walker, issued Mar. 7, 1978, which is incorporated herein by reference in its entirety.

An anti-viral agent can be present in an amount of from about 0.025% to about 5%, preferably from about 0.05% to about 2.5%, of the lotion. Suitable anti-viral agents include those effective against, or at least retardant toward Corona virus, Picorna virus, Rhino virus, Herpes simplex, Herpes genitalis, Herpes labialis, Respiratory Syncytial Virus [RSV], Para influenza, Cytomegalovirus, Adenovirus, Condyloma and certain synergistic disease states that can involve a virus and a protozoa or a virus and any of the unfriendly enzymes, e.g., protease, lipase and amylase, that causes a compromised skin as the precursor state for the viral infection to occur. Specific anti-viral agents suitable for use in the lotion of the present invention include bioflavonoids such as hesperitin, naringin, catechin and certain selected amino acids such as L-lysine and L-glutamic acid, a non-protein amino acid of leguminous origin such as L-canavanine and an analog of L-arginine; dicarboxylic acids such as malonic, glutaric, citric, succinic, and diglycolic acids; alpha hydroxy carboxylic acid such as D-galacturonic acid from Sterculia urens; neem seed oil [*Azadirachta indica*] in its un-denatured form; sandalwood oil [*Santalum album* L.] in its un-denatured form. Optionally, the anti-viral agent could be admixed with at most about 50% by weight of the anti-viral agent of a protease inhibitor such as zinc oxide or other suitable zinc salt.

The lotion can optionally include fragrance. The fragrance can be present in an amount of from about 0.01% to about 2%. Suitable fragrance includes volatile aromatic esters, non-aromatic esters, aromatic aldehydes, non-aromatic aldehydes, aromatic alcohols, non-aromatic alcohols, heterocyclic aroma chemicals, and natural floral fragrances, such as blossom, carnation, gardenia, geranium, iris, hawthorne, hyacinth and jasmin.

The lotion can optionally include natural or synthetic powder like talc, mica, boron nitride, silicone, or mixtures thereof.

During use as a dry product, the lotion of the present invention is transferred from the substrate, such as tissue, wipe, or nonwoven material to the user's skin and leaves a smooth-feeling, nongreasy layer which retards the loss of skin moisture otherwise known as trans-epidermal water loss (TEWL). The term TEWL generally refers to the rate of water vapor diffusion across the stratum corneum and would depend directly on the ambient relative humidity, the stratum corneum barrier integrity, temperature, and inversely on the stratum corneum thickness. TEWL (gram/meter$^2$*hour) can be determined by an evaporimeter based on the equation:

$$TEWL = D' dp/dn$$

where $D'$=constant (g/m*hr*Pa)

$dp/dn$=vapor pressure gradient (Pa/m)

p=vapor pressure (Pa)

n=distance from the skin (m)

See "Bioengineering of the skin, methods and instrumentation" page 2, which is incorporated by reference herein in its entirety.

Typically, TEWL can be reduced by applying an occlusive barrier agent, such as petrolatum. Petrolatum has several disadvantages, including effectively preventing moisture evaporation from the skin surface. Petrolatum is impermeable to moisture and may cause excessive skin hydration to result from water transfer from lower layers of skin. Excessive moisture retention by the epidermis can lead to swelling or edema and is to be avoided. Additionally, a highly occlusive barrier layer that inhibits oxygen exchange with the stratum corneum favors growth of anaerobic organisms on the skin whose acidic metabolic by-products can cause skin irritation and dermatitis. Consequently, to maintain proper skin health and conditioning, the skin surface needs to be able to exchange moisture as well as oxygen. Maintenance of proper oxygen exchange and moisture balance at the skin surface leads to a balanced population of aerobic and anaerobic microorganisms. The lotionized substrate of the invention is capable of providing a layer that acts to maintain the proper skin moisture/vapor balance.

When used as a prewetted product, water activates the ingredients in the lotion formulation containing surfactant to form a rinseable "cold-cream" type lotion. This cold-cream cleans better than water alone and is soothing to irritated skin tissues, such as inflamed hemorrhoidal tissues. In one embodiment, it is believed that the soothing action comes from the combination of rapidly spreading emollient and mild, non-irritating surfactants. The cold-cream is easily wiped away with a dry tissue of the invention to transfer a residual nongreasy layer that leaves the skin feeling silky smooth and refreshed.

The substrate web of the present invention optionally includes a wet strength agent. The wet strength agent includes temporary as well as permanent wet strength agents. Suitable wet strength agents include glyoxal; glutaraldehyde; uncharged chemical moieties selected from a group consisting of dialdehydes, aldehyde-containing polyols, uncharged aldehyde-containing polymers, and cyclic ureas and mixtures thereof, and aldehyde-containing cationic starch; mixtures of polyvinyl alcohol and salts of multivalent anions, such as boric acid or zirconium ammonium carbonates; glyoxalated polyacrylamide; polyamide-epichlorohydrin; polyamine-epichlorohydrin; urea-formaldehyde; melamine-formaldehyde; polyethyleneimine; and latex emulsions.

With respect to the lotionized substrate used premoistened with water, the substrate preferably exhibits an initial normalized cross direction (CD) wet tensile strength of at least about 25 grams/inch as measured using the Finch Cup method for an 18.5 lb/3000 sq. ft. ream and a Wet Abrasion Resistance Number (WARN) of at least about 4. Lotionized substrates of the present invention, such as tissues can exhibit a substantial ability to resist wet abrasion thereby enabling them to be used premoistened for effective cleansing. To evaluate the ability of a substrate, such as a tissue, to resist wet abrasion and to quantify the degree of pilling when a moistened tissue is wetted and rubbed, we employ the following test using a Sutherland Rub tester to reproducibly rub tissue over a pigskin surface which is considered to be a fair substitute for human skin, the similarity being noted in U.S. Pat. No. 4,112,167, which is incorporated herein by reference in its entirety. Four sheets of tissue are severed from a roll of tissue. The sheets are stacked so that the machine direction in each sheet is parallel to that of the others. By use of a paper cutter, the sheets are cut into specimens 2 inches in width and 4.5 inches in length.

A pigskin is stretched over the rubbing surface of a Sutherland Rub tester which is described in U.S. Pat. No. 2,734,375, which is incorporated herein by reference in its entirety. The pigskin is preconditioned by spraying a mist of demineralized water at neutral pH from a mist spray bottle until the pigskin is saturated. However, care should be taken to ensure that no excess water, or puddling, remains on the surface of the pigskin. A sponge is positioned in a tray and the tray is filled with ¾ inch of demineralized neutral pH water. A smooth blotter stock is positioned on the top of the sponge.

A specimen is clamped between two clamps at each end of a transparent plexiglas rub block which is adapted to be removably secured to moving arm of the Sutherland Rub tester, the clamps being positioned to hold the sheet to be tested against the rubbing surface of the rub block by wrapping the specimen around the lower portion of the block with the machine direction of the sample parallel to the direction of movement of the rubbing arm. The rub block with the specimen is placed onto the smooth surface of the blotter stock. The specimen is carefully watched through the transparent rub block until the specimen is saturated with water, at which point, the rub block with the specimen is removed from the blotter stock. At this stage, the specimen will be sagging since it expands upon wetting. The sag is removed from the specimen by opening a clamp on the rub block permitting the operator to ease the excess material into the clamp, removing the sag and allowing the sample to be thereafter reclamped so that it conforms to the lower surface of the rub block, the length of wet material matching the distance between the two clamps.

The Sutherland Rub tester is set for the desired number of strokes. The pigskin is moistened by using three mist applications of water from the spray bottle. After the water is absorbed into the pigskin and no puddles are present, the transparent rub block bearing the specimen is affixed to the arm of the Sutherland Rub tester and the specimen brought into contact with the pigskin. Upon activation, the specimen is rubbed against the pigskin for the predetermined desired number of strokes. Normally, only a few seconds, ideally less than about 10 seconds will elapse between first wetting the tissue and activation of the Sutherland Rub Tester. Thereafter, the specimen is detached from the Sutherland Rub tester and evaluated to determine the condition of the specimen, particularly whether pilling, shredding or balling of tissue on the rub block has occurred. Thereafter, the pigskin surface and the rub block are cleaned to prepare for the next specimen. For convenience, the WARN is defined as being the number of strokes that the specimen will endure on this test before pilling is observed on the pigskin. For use when premoistened with water, preferred are substrates having a WARN of at least about 4, more preferably at least about 8. For toweling, preferred are substrates having a WARN of at least about 8, more preferably at least about 15.

Optionally, the invention can include sensory signaling agents for the lotionized substrate. When used dry, the lotionized substrate, such as a tissue has a feeling of lubriciousness or skin smoothing action. However, when prewetted with water, as when using wetted bath tissue for cleaning sensitive perineal tissue, the lubricious feel may be less evident or absent even though the lotion is being transferred to the skin surface. In the latter situation, a sensory signaling agent present in the lotionized tissue would undergo a "water-activation" step to enhance the user's perception of the performance of the treated tissue.

The sensory signaling agent may generate a variety of effects, such as, effervescence, color change, foaming, production of a milky-white emulsion, feeling of a lubricious ointment or a moisture-containing gel, and the like. The signaling agent can be prepared or selected from polysaccharides, coacervates of anionic and cationic polymers, cross-linked hydrophilic polymers, or water soluble capsules containing gas generating agents, such as, separately encapsulated acid and a carbonate or bicarbonate compound, or compounds such as thermochromic liquid crystals which react to generate a color when the tissue is moistened with water.

The lotion composition can include other optional components typically present in lotions of this type. These optional components include a botanical extract, such as aloe extract, avocado oil, basil extract, sesame oil, olive oil, chamomile extract, eucalyptus extract, peppermint extract, as well as animal oil and mink oil, and the like. The lotion of the present invention can also optionally include a humectant. Humectants are hygroscopic materials with a two-fold moisturizing action including water retention and water absorption. Humectants prevent the loss of moisture from skin and help to attract moisture from the environment. Preferred humectants include glycerol, hydrolyzed silk, ammonium lactate, hydroxypropyltrimonium hydrolyzed silk, hydroxypropyl chitosan, hydroxypropyltrimonium hydrolyzed wheat protein, lactamidopropyltrimonium chloride, and ethyl ester of hydrolyzed silk. The botanical extract, animal oil or humectant is preferably present in an amount of less than about 3% when used in the base formulation of the invention. Further optional components include a skin refreshing agent such as encapsulated water in oil, eucalyptus oil, and menthol oil. All of these optional materials are well known in the art as additives for such formulations and can be employed in appropriate amounts in the lotion compositions of the present invention by those skilled in the art.

The substrate of the present invention can be any suitable applicator that the lotion can be retained upon. Suitable substrates include a web, gauze, cotton swab, transdermal patch, container or holder. The lotion may be retained on the substrate in any desired amount.

The web of the present invention can be any suitable substrate web, including a flushable or nonflushable web of cellulosic fibers; a web of synthetic fibrous material; tissue, towel or napkin, optionally wet-strengthened; wipe or non-woven material, such as that used for diaper, incontinence and menstrual pad cover-stock; and the like. Suitable synthetic fibrous material includes meltblown polyethylene, polypropylene, copolymers of polyethylene and polypropylene, bicomponent fibers including polyethylene or polypropylene, and the like. The substrate also may be embossed.

The present invention includes a flushable or nonflushable web of cellulosic fibers treated on at least one side thereof, preferably in an amount of from about 0.1% to about 25%, more preferably from about 0.5% to about 20%, by weight of the dried fiber web with the lotion of the present invention. The present invention further relates to a web of synthetic fibrous material treated on at least one side thereof, preferably in an amount of from about 0.1% to about 25%, more preferably from about 0.5% to about 20%, by weight of the dried web with the lotion of the present invention.

The substrate can be prepared according to conventional processes (including TAD, CWP and variants thereof) known to those skilled in the art. The substrate may be creped or uncreped. For example, conventional wet pressed tissues are typically prepared by first preparing and mixing the fibrous raw material in a vat. The stock is transferred usually at a consistency of about 1% to about 5% through a centrifugal pump to a headbox, where the consistency is about 0.1% to about 1.0%. The fibrous mixture is deposited into a moving foraminous wire such as fourdrinier wire to form a web mat. Water is drained through this wire by use of vacuum and drainage elements. The embryonic web is transferred onto a hot Yankee dryer via one or two press rolls. The web is about 25% to about 50% solids after passing through the press rolls. The transferred web is adhered onto the surface of the Yankee which has been previously prepared by spraying an adhesive material directly onto the metal surface. The dried web is then removed via the use of a creping doctor which scrapes off the web from the surface of the Yankee dryer metal drum. The dried web is then wound up at the reel of the paper machine. Lotion can be applied to the substrate according to conventional application methods known to those skilled in the art.

The invention will be further illustrated with reference to the following specific examples. It is understood that these examples are given by way of illustration and are not meant to limit the disclosure or the claims to follow.

EXAMPLES

The lotion formulations compiled in Tables 3 and 4 below were prepared according to the following procedure: the individual ingredients were mixed together and heated to about 75° C. until the mixture was completely melted. The mixture was maintained at about 75° C. for about 15 minutes with moderate agitation. At this point the lotion was ready to apply to a substrate.

DSC data were determined using a Perkin-Elmer DCS4, which had been calibrated with an indium metal standard, which has a melting (onset) temperature of 156.6° C. and a heat of melting of 6.80 calories per gram, as reported in the chemical literature. Each sample was placed into an analysis pan at room temperature, inserted into the instrument, cooled to −45° C., then taken through a three-step, heat/quick cool/heat, regimen at a heating rate of about 10° C. per minute through a range of from −45° C. to 100° C. and the data from the first heating was discarded. First-heating data are discarded because sample contact with the DSC pan is poor and peaks seen are often due to samples shifting in the pan. Each formulation was contained in a 300 mL beaker, samples were taken from three locations, edge/center/edge in a straight line. A slight variation in composition was observed between the edge and center samples. Additionally, standard DSC operating parameters known to those skilled in the art were used for all examples. DSC thermograms from the second heat cycle were used for all analyses. A sample size typically of about 14 milligrams was used for each formulation example. The energy required to melt each sample from a temperature of −45° C. is designated as the total energy to melt (ΔH total); the energy required to raise the temperature of the sample from −45° C. to either 30° C. or 37° C. is the ΔH below 30° C. or ΔH below 37° C., respectively; and the energy required to raise the temperature of the sample from 30° C. or 37° C. to fully liquid is the ΔH above 30° C. or ΔH above 37° C., respectively.

TABLE 3

| # | Chemicals | Example 1 (weight %) | Example 2 (weight %) | Example 3 (weight %) | Example 4 (weight %) | Example 5 (weight %) | Example 6 (weight %) | Example 7 (weight %) | Example 8 (weight %) |
|---|---|---|---|---|---|---|---|---|---|
| 1 | Mineral oil | 30 | 0 | 0 | 17.5 | 0 | 0 | 0 | 0 |
| 2 | Heavy mineral oil | 0 | 0 | 60 | 0 | 0 | 0 | 0 | 0 |
| 3 | Petrolatum | 65 | 48.4 | 0 | 0 | 0 | 0 | 0 | 0 |
| 4 | Isopropyl palmitate | 0 | 0 | 3 | 0 | 0 | 0 | 0 | 0 |
| 5 | C12–C15 Alkyl octanoate | 0 | 0 | 0 | 0 | 35 | 0 | 0 | 0 |
| 6 | C12 . C15 Alkyl benzoate | 0 | 0 | 0 | 17.5 | 0 | 35 | 0 | 17.5 |

TABLE 3-continued

| # | Chemicals | Example 1 (weight %) | Example 2 (weight %) | Example 3 (weight %) | Example 4 (weight %) | Example 5 (weight %) | Example 6 (weight %) | Example 7 (weight %) | Example 8 (weight %) |
|---|---|---|---|---|---|---|---|---|---|
| 7 | n-Stearyl benzoate | 0 | 0 | 0 | 0 | 0 | 0 | 35 | 17.5 |
| 8 | Ceresin wax | 0 | 0 | 18 | 0 | 0 | 0 | 0 | 0 |
| 9 | Cetearyl alcohol | 0 | 0 | 18 | 65 | 65 | 65 | 65 | 65 |
| 10 | Dimethicone | 0 | 0 | 1 | 0 | 0 | 0 | 0 | 0 |
| 11 | Brij 72 | 5 | 0 | 0 | 0 | 0 | 0 | 0 | |
| 12 | Brij 76 | 0 | 29.1 | 0 | 0 | 0 | 0 | 0 | 0 |
| 13 | Tween 61 | 0 | 15 | 0 | 0 | 0 | 0 | 0 | 0 |
| 14 | Glycomul S-CG5 | 0 | 6.5 | 0 | 0 | 0 | 0 | 0 | 0 |
| ΔH Total (cal/g) | | 9 | 12 | 16 | 36 | 33 | 38 | 42 | 40 |
| ΔH below 30° C. (cal/g) | | 7 | 4 | 6 | 15 | 15 | 15 | 6 | 19 |
| ΔH above 30° C. (cal/g) | | 2 | 8 | 10 | 21 | 18 | 23 | 36 | 21 |
| ΔH below 37° C. (cal/g) | | 8 | 11 | 10 | 20 | 21 | 21 | 21 | 24 |
| ΔH above 37° C. (cal/g) | | 1 | 1 | 6 | 16 | 12 | 17 | 21 | 16 |
| Onset Temperature (°C.) | | 3 | 28 | 25 | 35 | 31 | 35 | 31 | 36 |
| Greasiness Sensory Panel Index | | 2.45 | 1.43 | 1.36 | 0.23 | 0.23 | 0.26 | 0.01 | 0.21 |
| Hand feel perception | | Very greasy | Greasy | Greasy | Non greasy | Non greasy | Non greasy | Non greasy | Non greasy |

TABLE 4

| Examples | 9 | 10 | 11 | 12 | 13 | 14 | 15 | 16 | 17 | 18 | 19 | 20 |
|---|---|---|---|---|---|---|---|---|---|---|---|---|
| Cetearyl alcohol (%) | 100 | 90 | 85 | 80 | 75 | 65 | 55 | 50 | 45 | 40 | 25 | 0 |
| Mineral oil (%) | 0 | 10 | 15 | 20 | 25 | 35 | 45 | 50 | 55 | 60 | 75 | 100 |
| ΔH total (cal/g) | 49 | 46 | 45 | 43 | 38 | 34 | 30 | 26 | 25 | 23 | 13 | 3 |
| ΔH < 30° C. (cal/g) | 8 | 13 | 15 | 13 | 11 | 12 | 11 | 10 | 11 | 11 | 7 | 3 |
| ΔH > 30° C. (cal/g) | 41 | 33 | 30 | 30 | 27 | 22 | 19 | 16 | 14 | 12 | 6 | 0 |
| ΔH < 37° C. (cal/g) | 15 | 17 | 19 | 18 | 15 | 17 | 16 | 15 | 16 | 16 | 12 | 3 |
| ΔH > 37° C. (cal/g) | 34 | 29 | 26 | 25 | 23 | 17 | 14 | 11 | 9 | 7 | 1 | 0 |
| Onset temperature °C. | 49 | 45 | 42 | 42 | 39 | 35 | 34 | 32 | 28 | 28 | 28 | −42 |
| Hand feel perception | solid | non greasy | non greasy | non greasy | non greasy | non greasy | non greasy | less greasy | greasy | greasy | greasy | greasy |

Examples 1 to 3, 9 and 17 to 20 are Comparative and not in accordance with the present invention. Examples 4 to 8 and 10 to 16 were prepared in accordance with the present invention and had a better hand feel perception and were perceived as feeling significantly less greasy than the lotions prepared in Comparative Examples 1 to 3 and 17 to 19. The Greasiness Sensory Panel Index was determined by a group of sensory panelists who directly compared each lotion formulation to each other lotion formulation in paired comparison fashion. Each lotion was applied on a 1 inch by 3 inch piece of a coated paperboard with an equal quantity of each lotion. Each lotion sample was held stationary between the forefinger and thumb, with the treated side facing the thumb, for a period of five seconds. After five seconds, the sample was set down, then the thumb and forefinger were rubbed together to determine how greasy each lotion felt. Before testing, as well as in between each sample pair, panelists washed their fingers in soapy water, rinsed them with clean water, and dried them thoroughly. The paired comparison results were used as input for the Thurstone transformation algorithm (see "A Law Of Comparative Judgment", L. L. Thurstone, University of Chicago, 1927). The algorithm yielded relative magnitudes of difference between the lotion formulations for perceived greasiness. A low value of Greasiness Index means the lotion felt less greasy, and a difference between Greasiness Index of 0.40 or greater is significant at the 95% confidence level.

Sensory perceived greasiness is surprisingly well correlated to the onset of melting temperature. The data in Table 3 shows that lotions having onset of melting temperatures from about 31° C. through about 36° C. (Examples 4 to 8) exhibit a nongreasy hand feel perception compared to the comparative lotions that have an onset of melting temperature of about 3° C. through about 28° C. (Comparative Examples 1 to 3). This correlation indicates that the onset of melting temperature for the lotion is important to hand feel perception. Hand feel perception was performed according to the same protocol as that for the Greasiness Index. Hand feel perception was determined on a scale of very greasy, greasy, less greasy, and non greasy. Of course, there may be various levels of greasiness within each of these designations.

TABLE 5

| # | Chemicals | Example 21 Weight (%) | Example 22 Weight (%) | Example 23 Weight (%) |
|---|---|---|---|---|
| 1 | C12–C15 Alkyl benzoate | 30 | 0 | 0 |
| 2 | n-Stearyl benzoate | 0 | 30 | 0 |
| 3 | Poloxamer 182 dibenzoate | 0 | 0 | 30 |
| 4 | Cetearyl alcohol | 57 | 57 | 57 |
| 5 | Glucate SS (methyl glucose sesquistearate) | 3 | 3 | 3 |
| 6 | Glucamate SSE-20 (PEG-20 methyl glucose sesquistearate) | 10 | 10 | 10 |
| | ΔH Total (cal/g) | 32 | 40 | 30 |
| | ΔH below 30° C. (cal/g) | 15 | 11 | 10 |
| | ΔH above 30° C. (cal/g) | 17 | 29 | 20 |
| | ΔH below 37° C. (cal/g) | 19 | 26 | 13 |
| | ΔH above 37° C. (cal/g) | 13 | 14 | 17 |
| | Onset Temperature (°C.) | 34 | 36 | 43 |
| | Greasiness Sensory Panel Index | 0.18 | 0 | NA |
| | Hand feel perception | Non greasy | Non greasy | Non greasy |

Examples 21 to 23 were prepared in accordance with the present invention. These examples include lotion formulations containing an emollient, retention/release agent, and a surfactant pair. These lotions were prepared by mixing together the ingredients and heating up to 75° C. until the mixture was completely melted. The invention formulations from Examples 21 to 23 clearly performed better than the comparative formulations, as shown by very low Greasiness Sensory Panel Index values.

TABLE 6

| # | Chemicals | Example 24 (weight %) | Example 25 (weight %) | Example 26 (weight %) | Example 27 (weight %) |
|---|---|---|---|---|---|
| 1 | C12–C15 Alkyl benzoate | 30 | 30 | 30 | 30 |
| 2 | Cetearyl alcohol | 56 | 56 | 56 | 56 |
| 3 | Glucate SS (methyl glucose sesquistearate) | 3 | 3 | 3 | 3 |
| 4 | Glucamate SSE-20 (PEG-20 methyl glucose sesquistearate) | 10 | 10 | 10 | 10 |
| 5 | Phospholipid CDM | 1 | 0 | 0 | 0 |
| 6 | 2,4,4'-Trichloro-2'-hydroxydiphenyl ether | 0 | 1 | 0 | 0 |
| 7 | α-Hydroxyquinoline | 0 | 0 | 1 | 0 |
| 8 | 1,3-Bis(hydroxymethyl)-5,5-dimethylhydantoin + 3-iodo-2-propynyl butyl carbamate | 0 | 0 | 0 | 1 |

Examples 24 to 27 were prepared in accordance with the present invention. These lotion formulations contain surfactants and an antimicrobial agent. Antimicrobial agents were melted in the base lotion at a temperature of from about 65° C. to about 85° C. (depending on the melting point of each antimicrobial agent), after the base lotion was completely melted at 65° C.

Example 28

The lotion formula prepared in Example 21 was applied to one side of a creped 2-ply tissue paper at a temperature of from about 50° C. to about 55° C. Application of the formulation to the substrate was made via a heated anilox roll and a backing impression rubber roll. The melted composition was supplied from a heated tank containing the formulation and pumped to a heated enclosed doctor cavity chamber. The composition was applied directly through the cavity applicator into the cells of the anilox roll. The anilox roll used in this Example was a laser engraved ceramic roll supplied by Praxair. The anilox roll had a line screen of 400 per lineal inch and a theoretical volume of 3.5 billion cubic microns (BCM) per square inch of roll surface. The rubber impression roll had a 65 shore A durometer. The paper was passed directly between the engraved anilox roller and the rubber impression roll at a nip width of 0.34 inches. The heated anilox roll, the impression rubber roll and the line speed was 500 fpm. The treated paper was subsequently embossed and converted into small consumer size rolls. The resulting lotionized bath tissue had a lubricious and nongreasy feel.

Example 29

The melted lotion composition prepared in Example 21 was applied similarly to a 1-ply basesheet containing 6% glyoxal temporary wet strength, supplied by Hoechst-Celanese Chemical Company, in a similar manner as that in Example 28. The resultant lotionized tissue was wetted and wiped on the skin and found to transfer a smooth, lubricious, nongreasy feel to the skin.

Example 30

Example 30 illustrates that the lotion composition of the present invention can be applied to one side or both sides of a bathroom tissue product. The first tissue was a 2-ply control tissue with no applied lotion. The second tissue was a 2-ply tissue where lotion was applied to only one ply (before the plies were joined) using a heated engraved anilox roll. The third tissue was a 2-ply tissue where lotion was applied to only one ply (before the plies were joined) using a heated engraved anilox roll. The fourth tissue was a 2-ply tissue where lotion was applied to both the plies (before the plies were joined) using a heated engraved anilox roll.

What is claimed is:

1. A substrate treated with a nongreasy lotion comprising: an emollient and a retention/release agent, wherein said lotion comprises a ΔH above about 37° C. of above about 10 calories/gram, a total heat of melting of above about 25 calories/gram, and an onset of melting temperature of at least about 30° C.

2. The substrate according to claim 1, wherein said lotion is at least partially solid at about room temperature and at least partially liquid at about human skin temperature.

3. The substrate according to claim 1, wherein said total heat of melting is above about 30 calories/gram.

4. The substrate according to claim 1, wherein said lotion further comprises a ΔH below about 37° C. of above about 15 calories/gram.

5. The substrate according to claim 1, wherein said onset of melting temperature is within the range of from about 30° C. to about 45° C.

6. The substrate according to claim 1, wherein said lotion further comprises a surfactant.

7. The substrate according to claim 6, wherein said surfactant comprises a hydrophilic lypophilic balance value of less than about 8.

8. The substrate according to claim 6, wherein said surfactant comprises a hydrophilic lypophilic balance value of greater than about 13.

9. The substrate according to claim 6, wherein said surfactant comprises a surfactant blend capable of emulsifying oil in water or water in oil.

10. The substrate according to claim 9, wherein said surfactant blend comprises methyl glucoside sesquistearate and ethoxylated methyl glucoside sesquistearate containing 20 moles of oxyethylene units.

11. The substrate according to claim 1, wherein said lotion further comprises an medicinal agent.

12. The substrate according to claim 11, wherein said medicinal agent comprises an antimicrobial agent.

13. The substrate according to claim 12, wherein said antimicrobial agent comprises triclosan, triclocarban, chloroxylenol, a mixture of 1,3-bis(hydroxymethyl)-5,5-dimethylhydantoin and 3-iodo-2-propynyl butyl carbamate, butylparaben, ethylparaben, methylparaben, oxyquinoline, methylchloroisothiazoline, coco phosphatidyl PG-dimonium chloride, methylisothiazoline, quaternary ammonium compounds, or mixtures thereof.

14. The substrate according to claim 12, wherein said antimicrobial agent is triclosan.

15. The substrate according to claim 1, wherein said lotion further comprises fragrance.

16. The substrate according to claim 1, wherein said substrate comprises an applicator, a web, gauze, cotton swab, transdermal patch, container or holder.

17. The substrate according to claim 16, wherein said web comprises a flushable or nonflushable web of cellulosic fibers treated with an amount of said lotion of from about 0.1% to about 25% by weight of the dry web.

18. The substrate according to claim 17, wherein said web comprises an initial normalized cross direction wet tensile strength of at least about 25 grams/inch as measured using the Finch Cup method and a Wet Abrasion Resistance Number of at least about 4.

19. The substrate according to claim 17, wherein said web further comprises a wet strength agent.

20. The substrate according to claim 19, wherein said wet strength agent comprises: glyoxal; glutaraldehyde; uncharged chemical moieties selected from a group consisting of dialdehydes, aldehyde-containing polyols, uncharged aldehyde-containing polymers, and cyclic ureas and mixtures thereof; aldehyde-containing cationic starch; glyoxalated polyacrylamide; latex emulsions; polyamide-epichlorohydrin; polyamine-epichlorohydrin; urea-formaldehyde; melamine-formaldehyde; polyethyleneimine; mixtures of polyvinyl alcohol and salts of multivalent anions; or mixtures thereof.

21. The substrate according to claim 16, wherein said web comprises a synthetic fibrous material treated with an amount of said lotion of from about 0.1% to about 25% by weight of the dry web.

22. A substrate treated with a nongreasy lotion comprising: an emollient and a retention/release agent, wherein said lotion comprises a ΔH above about 30° C. of above about 15 calories/gram, a ΔH below about 30° C. of above about 10 calories/gram, a total heat of melting of above about 25 calories/gram, and an onset of melting temperature of at least about 30° C.

23. The substrate according to claim 22, wherein said lotion is at least partially solid at about room temperature and at least partially liquid at about human skin temperature.

24. The substrate according to claim 22, wherein said total heat of melting is above about 30 calories/gram.

25. The substrate according to claim 22, wherein said onset of melting temperature is within the range of from about 30° C. to about 45° C.

26. The substrate according to claim 22, wherein said lotion further comprises a surfactant.

27. The substrate according to claim 26, wherein said surfactant, comprises a hydrophilic lypophilic balance value of less than about 8.

28. The substrate according to claim 26, wherein said surfactant comprises a hydrophilic lypophilic balance value of greater than about 13.

29. The substrate according to claim 26, wherein said surfactant comprises a surfactant blend capable of emulsifying oil in water or water in oil.

30. The substrate according to claim 29, wherein said surfactant blend comprises methyl glucoside sesquistearate and ethoxylated methyl glucoside sesquistearate containing 20 moles of oxyethylene units.

31. The substrate according to claim 22, wherein said lotion further comprises an medicinal agent.

32. The substrate according to claim 31, wherein said medicinal agent comprises an antimicrobial agent.

33. The substrate according to claim 32, wherein said antimicrobial agent comprises triclosan, triclocarban, chloroxylenol, a mixture of 1,3-bis(hydroxymethyl)-5,5-dimethylhydantoin and 3-iodo-2-propynyl butyl carbamate, butylparaben, ethylparaben, methylparaben., oxyquinoline, methylchloroisothiazoline, coco phosphatidyl PG-dimonium chloride, methylisothiazoline, quaternary ammonium compounds, or mixtures thereof.

34. The substrate according to claim 32, wherein said antimicrobial agent is triclosan.

35. The substrate according to claim 22, wherein said lotion further comprises fragrance.

36. The substrate according to claim 22, wherein said substrate comprises an applicator, a web, gauze, cotton swab, transdermal patch, container or holder.

37. The substrate according to claim 36, wherein said web comprises a flushable or nonflushable web of cellulosic fibers treated with an amount of said lotion of from about 0.1% to about 25% by weight of the dry web.

38. The substrate according to claim 37, wherein said web comprises an initial normalized cross direction wet tensile strength of at least about 25 grams/inch as measured using the Finch Cup method and a Wet Abrasion Resistance Number of at least about 4.

39. The substrate according to claim 37, wherein said web further comprises a wet strength agent.

40. The substrate according to claim 39, wherein said wet strength agent comprises: glyoxal; glutaraldehyde; uncharged chemical moieties selected from a group consisting of dialdehydes, aldehyde-containing polyols, uncharged aldehyde-containing polymers, and cyclic ureas and mixtures thereof; aldehyde-containing cationic starch; glyoxalated polyacrylamide; latex emulsions; polyamide-epichlorohydrin; polyamine-epichlorohydrin; urea-formaldehyde; melamine-formaldehyde; polyethyleneimine; mixtures of polyvinyl alcohol and salts of multivalent anions; or mixtures thereof.

41. The substrate according to claim 36, wherein said web comprises a synthetic fibrous material treated with an amount of said lotion of from about 0.1% to about 25% by weight of the dry web.

42. A substrate treated with a nongreasy lotion obtained by mixing an emollient and a retention/release agent, wherein said lotion comprises a $\Delta H$ above about 37° C. of above about 10 calories/gram, a total heat of melting of above about 25 calories/gram, and an onset of melting temperature of at least about 30° C.

43. A substrate treated with a nongreasy lotion obtained by mixing an emollient and a retention/release agent, wherein said lotion comprises a $\Delta H$ above about 30° C. of above about 15 calories/gram, a $\Delta H$ below about 30° C. of above about 10 calories/gram, a total heat of melting of above about 25 calories/gram, and an onset of melting temperature of at least about 30° C.

44. The substrate according to claim 1, wherein said emollient is present in an amount of from at least about 5% by weight of the lotion.

45. The substrate according to claim 44, wherein said emollient is present in an amount of from about 5% to about 75%.

46. The substrate according to claim 45, wherein said emollient is present in an amount of from about 10% to about 55%.

47. The substrate according to claim 46, wherein said emollient is present in an amount of from about 15% to about 40%.

48. The substrate according to claim 1, wherein said retention/release agent is present in an amount of from about 25% to about 95% by weight of the lotion.

49. The substrate according to claim 48, wherein said retention/release agent is present in an amount of from about 45% to about 90%.

50. The substrate according to claim 1, wherein said emollient comprises an aromatic ester emollient or a fatty alcohol ester of a non-fatty organic acid emollient or mixture thereof.

51. The substrate according to claim 50, wherein said aromatic ester emollient comprises a benzoate ester emollient.

52. The substrate according to claim 50, wherein said fatty alcohol ester of a non-fatty organic acid emollient comprises $C_{12}$–$C_{15}$ octanoate.

53. The substrate according to claim 51, wherein said benzoate ester emollient comprises $C_{12}$–$C_{15}$ alkyl benzoate, stearyl benzoate, octyl dodecyl benzoate, isostearyl benzoate, methyl gluceth-20 benzoate, stearyl ether benzoate, poloxamer 182 dibenzoate, poloxamer 105 benzoate, or mixtures thereof.

54. The substrate according to claim 1, wherein said retention/release agent comprises a $C_{12}$–$C_{18}$ fatty alcohol.

55. The substrate according to claim 54, wherein said $C_{12}$–$C_{18}$ fatty alcohol comprises dodecanol, tridecanol, tetradecanol, pentadecanol, hexadecanol, heptadecanol, octadecanol, or mixtures thereof.

56. The substrate according to claim 1, wherein said lotion contains about 15% or less water.

57. The substrate according to claim 1, wherein said lotion contains about 10% or less water.

58. The substrate according to claim 1, wherein said lotion contains about 5% or less water.

59. The substrate according to claim 1, wherein said lotion is substantially free of water.

60. The substrate according to claim 22, wherein said emollient is present in an amount of from at least about 5% by weight of the lotion.

61. The substrate according to claim 60, wherein said emollient is present in an amount of from about 5% to about 75%.

62. The substrate according to claim 61, wherein said emollient is present in an amount of from about 10% to about 55%.

63. The substrate according to claim 62, wherein said emollient is present in an amount of from about 15% to about 40%.

64. The substrate according to claim 22, wherein said retention/release agent is present in an amount of from about 25% to about 95% by weight of the lotion.

65. The substrate according to claim 64, wherein said retention/release agent is present in an amount of from about 45% to about 90%.

66. The substrate according to claim 22, wherein said emollient comprises an aromatic ester emollient or a fatty alcohol ester of a non-fatty organic acid emollient or mixture thereof.

67. The substrate according to claim 66, wherein said aromatic ester emollient comprises a benzoate ester emollient.

68. The substrate according to claim 66, wherein said fatty alcohol ester of a non-fatty organic acid emollient comprises $C_{12}$–$C_{15}$ octanoate.

69. The substrate according to claim 67, wherein said benzoate ester emollient comprises $C_{12}$–$C_{15}$ alkyl benzoate, stearyl benzoate, octyl dodecyl benzoate, isostearyl benzoate, methyl gluceth-20 benzoate, stearyl ether benzoate, poloxamer 182 dibenzoate, poloxamer 105 benzoate, or mixtures thereof.

70. The substrate according to claim 22, wherein said retention/release agent comprises a $C_{12}$–$C_{18}$ fatty alcohol.

71. The substrate according to claim 70, wherein said $C_{12}$–$C_{18}$ fatty alcohol comprises dodecanol, tridecanol, tetradecanol, pentadecanol, hexadecanol, heptadecanol, octadecanol, or mixtures thereof.

72. The substrate according to claim 22, wherein said lotion contains about 15% or less water.

73. The substrate according to claim 22, wherein said lotion contains about 10% or less water.

74. The substrate according to claim 22, wherein said lotion contains about 5% or less water.

75. The substrate according to claim 22, wherein said lotion is substantially free of water.

* * * * *